(12) United States Patent
Reese

(10) Patent No.: US 7,022,833 B2
(45) Date of Patent: Apr. 4, 2006

(54) PROCESS FOR THE PREPARATION OF PHOSPHOROTHIOATE TRIESTERS

(75) Inventor: Colin Bernard Reese, London (GB)

(73) Assignee: Avecia Limited, Manchester (GB)

( * ) Notice: Subject to any disclaimer, the term of this patent is extended or adjusted under 35 U.S.C. 154(b) by 337 days.

(21) Appl. No.: 10/220,353

(22) PCT Filed: Feb. 23, 2001

(86) PCT No.: PCT/GB01/00764

§ 371 (c)(1),
(2), (4) Date: Aug. 29, 2002

(87) PCT Pub. No.: WO01/64702

PCT Pub. Date: Sep. 7, 2001

(65) Prior Publication Data

US 2003/0099981 A1 May 29, 2003

(30) Foreign Application Priority Data

Mar. 1, 2000 (GB) .............................. 0004889

(51) Int. Cl.
C07H 21/00 (2006.01)
C07H 21/02 (2006.01)
C07H 21/04 (2006.01)

(52) U.S. Cl. ................ 536/25.3; 536/25.33; 536/25.34; 536/22.1; 536/23.1

(58) Field of Classification Search ................ 536/25.3, 536/25.33, 25.34, 22.1, 23.1
See application file for complete search history.

(56) References Cited

U.S. PATENT DOCUMENTS 6,506,894 B1 * 1/2003 Reese et al. ............... 536/25.3

FOREIGN PATENT DOCUMENTS

| EP | 0 723 973 A1 | 7/1996 |
| WO | WO 98/54198 | 12/1998 |
| WO | WO 99/09041 | 2/1999 |
| WO | WO 01/27126 A1 | 4/2001 |

OTHER PUBLICATIONS

C. Reese et al., "Preparation of an Octadeoxyribonucleoside Heptaphosphorothioate by the Phosphotrieseter Approach in Solution". Nucleosides & Nucleotides, vol. 17(1–3), 1998, pp. 451–470.

P. J. Garegg et al., "Nucleoside Phosphonates: Part 7, Studies on the Oxidation of Nucleoside Phosphonate Esters". J. Chem. Soc. Perkin Trans. I, 1987, pp. 1269–1273, abstract.

* cited by examiner

Primary Examiner—James O. Wilson
Assistant Examiner—Howard V. Owens, Jr.
(74) Attorney, Agent, or Firm—Morgan, Lewis & Bockius LLP

(57) ABSTRACT

A process for the synthesis of a phosphorothioate triester is provided. The process comprises the coupling of an H-phosphonate with an alcohol in the presence of a solution comprising both a coupling agent and a sulfur transfer agent. Preferably, the H-phosphonate and alcohol are protected nucleosides or oligonucleotides.

30 Claims, No Drawings

PROCESS FOR THE PREPARATION OF PHOSPHOROTHIOATE TRIESTERS

The present invention provides a method of synthesising phosphorothioate triesters, particularly oligonucleotides and including oligonucleotide phosphorothioates.

In the past 15 years or so, enormous progress has been made in the development of the synthesis of oligodeoxyribonucleotides (DNA sequences), oligoribonucleotides (RNA sequences) and their analogues. The increased interest in the therapeutic applications of DNA and RNA sequences has led to increasing demand for larger quantities of material, and a great deal of work has been carried out on the scaling-up of oligonucleotide synthesis. Virtually all of this work has involved building larger and larger synthesisers and using the same phosphoramidite chemistry on a solid support. An alternative procedure for the synthesis of oligonucleotides is disclosed in International Patent Application WO99/09041. The procedure disclosed employs sequential coupling and sulfur transfer steps in solution.

According to a first aspect of the present invention, there is provided a process for the preparation of a phosphorothioate triester which comprises coupling an H-phosphonate with an alcohol in the presence of a coupling agent thereby to form an H-phosphonate diester, and subsequently, the H-phosphonate diester is reacted with a sulfur transfer agent thereby to form a phosphorothioate triester, characterised in that the coupling reaction between the H-phosphonate and the alcohol, occurs in the presence of the sulfur transfer agent.

In many preferred embodiments it is envisaged that reaction proceeds by a sequence whereby the H-phosphonate reacts with the alcohol in the presence of the coupling agent and the H-phosphonate diester formed in situ reacts rapidly with the sulfur transfer agent which is also present, as shown by way of example in the reaction scheme:

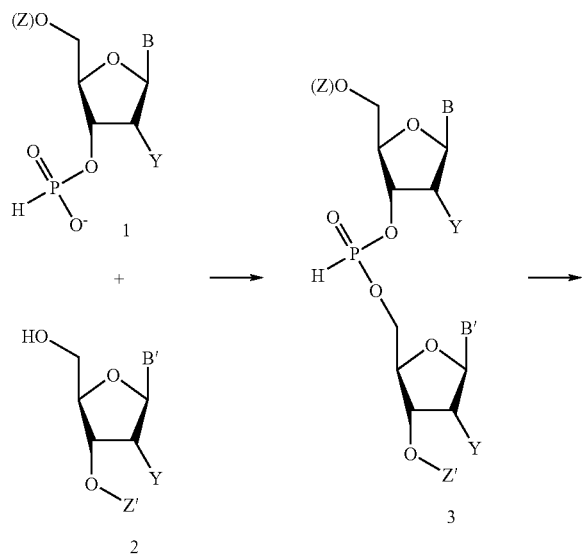

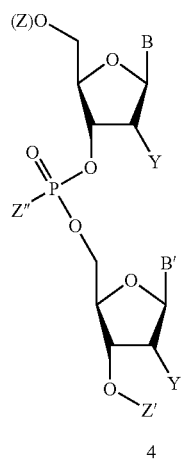

wherein Z, Z' and Z" independently represent protecting groups, B and B' independently are nucleobases, and each Y independently represents H, O-alkyl, O-alkenyl, O-protecvting group, C-alkyl or C-alkenyl.

The H-phosphonate employed in the process of the present invention is advantageously a protected nucleoside or oligonucleotide H-phosphonate, or an analogue thereof, preferably comprising a 5' or a 3' H-phosphonate function, particularly preferably a 3' H-phosphonate function. Preferred nucleosides are 2'-deoxyribonucleosides and ribonucleosides; preferred oligonucleotides are oligodeoxyribonucleotides and oligoribonucleotides.

When the H-phosphonate is a protected deoxyribonucleoside, ribonucleoside, oligodeoxyribonucleotide or oligoribonucleotide derivative comprising a 3' H-phosphonate function, the 5' hydroxy function is advantageously protected by a suitable protecting group. Examples of such suitable protecting groups include acid labile protecting groups, particularly trityl and substituted trityl groups such as dimethoxytrityl and 9-phenylxanthen-9-yl groups; and base labile-protecting groups such as FMOC.

When the H-phosphonate building block is a protected deoxyribonucleoside, ribonucleoside, oligodeoxyribonucleotide or oligoribonucleotide derivative comprising a 5' H-phosphonate function, the 3' hydroxy function is advantageously protected by a suitable protecting group. Suitable protecting groups include those disclosed above for the protection of the 5' hydroxy functions of 3' H-phosphonate building blocks and acyl, such as levulinoyl and substituted levulinoyl, groups.

When the H-phosphonate is a protected ribonucleoside or a protected oligoribonucleotide, the 2'-hydroxy function is advantageously protected by a suitable protecting group, for example an acid-labile acetal protecting group, particularly a 1-(aryl)-4-alkoxypiperidin-4-yl group such as 1-(2-fluorophenyl)-4-methoxypiperidin-4-yl (Fpmp) or 1-(2-chlorophenyl)-4-ethoxypiperidin-4-yl (Cpep); and trialkylsilyl groups, often tri($C_{1-4}$-alkyl)silyl groups such as a tertiary butyl dimethylsilyl group. Alternatively, the ribonucleoside or oligoribonucleotide may be a 2'-O-alkyl, 2'-O-alkoxyalkyl or 2'-O-alkenyl derivative, commonly a $C_{1-4}$ alkyl, $C_{1-4}$ alkoxy$C_{1-4}$alkyl or alkenyl derivative, in which case, the 2' position does not need further protection. H-phosphonates of nucleoside and oligonucleotide analogues that may be employed in the process of the present invention include 2'-fluoro, 2'-amino, 2'-C-alkyl and 2'-C-alkenyl substituted nucleoside and oligonucleotide derivatives.

Other H-phosphonates that may be employed in the process according to the present invention are derived from other polyfunctional alcohols, especially alkyl alcohols, and preferably diols or triols. Examples of alkyl diols include ethane-1,2-diol, and low molecular weight poly(ethylene glycols), such as those having a molecular weight of up to 400. Examples of alkyl triols include glycerol and butane triols. Commonly, only a single H-phosphonate function will be present, the remaining hydroxy groups being protected by suitable protecting groups, such as those disclosed hereinabove for the protection at the 5' or 2' positions of ribonucleosides.

The alcohol employed in the process of the present invention is commonly a protected nucleoside or oligonucleotide comprising a free hydroxy group, preferably a free 3' or 5' hydroxy group, and particularly preferably a 5' hydroxy group.

When the alcohol is a protected nucleoside or a protected oligonucleotide, preferred nucleosides are deoxyribonucleosides and ribonucleosides and preferred oligonucleotides are oligodeoxyribonucleotides and oligoribonucleotides.

When the alcohol is a deoxyribonucleoside, ribonucleoside oligodeoxyribonucleotide or oligoribonucleotide derivative comprising a free 5'-hydroxy group, the 3'-hydroxy function is advantageously protected by a suitable protecting group. Examples of such protecting groups include acyl groups, commonly comprising up to 16 carbon atoms, such as those derived from gamma keto acids, such as levulinoyl and substituted levulinoyl groups, and analogous groups. Substituted levulinoyl groups include particularly 5-halo-levulinoyl, such as 5,5,5-trifluorolevulinoyl; analogous groups include for example benzoylpropionyl groups. Other such protecting groups include fatty alkanoyl groups, including particularly linear or branched $C_{6-16}$ alkanoyl groups, such as lauroyl groups; benzoyl and substituted benzoyl groups, such as alkyl, commonly $C_{1-4}$ alkyl-, and halo, commonly chloro or fluoro, substituted benzoyl groups; and silyl ethers, such as alkyl, commonly $C_{1-4}$ alkyl, and aryl, commonly phenyl, silyl ethers, particularly tertiary butyl dimethyl silyl and tertiary butyl diphenyl silyl groups.

When the alcohol is a protected deoxyribonucleoside, ribonucleoside, oligodeoxyribonucleotides or oligoribonucleotide comprising a free 3'-hydroxy group, the 5'-hydroxy function is advantageously protected by a suitable protecting group. Suitable protecting groups are those disclosed above for the protection of the 5' hydroxy group of deoxyribonucleosides, ribonucleosides, oligodeoxyribonucleotides and oligoribonucleotide 3' H-phosphonates.

When the alcohol is a ribonucleoside or an oligoribonucleotide, the 2'-hydroxy function is advantageously protected by a suitable protecting group, such as an acetal protecting group, particularly a 1-(aryl)-4-alkoxypiperidin-4-yl group such as 1-(2-fluorophenyl)-4-methoxypiperidin-4-yl (Fpmp) or 1-(2-chlorophenyl)-4-ethoxypiperidin-4-yl (Cpep); and trialkylsilyl groups, often tri($C_{1-4}$-alkyl)silyl groups such as a tertiary butyl dimethyl silyl group. Alternatively, the ribonucleoside or oligoribonucleotide may be a 2'-O-alkyl, 2'-O-alkoxyalkyl or 2-'O-alkenyl derivative, commonly a $C_{1-4}$ alkyl, $C_{1-4}$ alkoxy$C_{1-4}$alkyl or alkenyl derivative, in which case, the 2' position does not need further protection. Nucleoside and oligonucleotide analogues that may be employed as alcohols in the process of the present invention include 2'-fluoro, 2'-amino, 2'-C-alkyl and 2'-C-alkenyl substituted nucleoside and oligonucleotide derivatives.

Other alcohols that may be employed in the process according to the present invention are non-saccharide polyols, especially alkyl polyols, and preferably diols or triols. Examples of alkyl diols include ethane-1,2-diol, and low molecular weight poly(ethylene glycols), such as those having a molecular weight of up to 400. Examples of alkyl triols include glycerol and butane triols. Commonly, only a single free hydroxy group will be present, the remaining hydroxy groups being protected by suitable protecting groups, such as those disclosed hereinabove for the protection at the 5' or 2' positions of ribonucleosides. However, more than one free hydroxy group may be present if it is desired to perform identical couplings on more than one hydroxy group.

When either or both of an oligonucleotide H-phosphonate or oligonucleotide comprising a free hydroxy group is employed, the internucleotide linkages, which may comprise phosphate, phosphorothioate or both phosphate and phosphorothioate linkages, are preferably protected. Examples of such protecting groups are well known in the art and include aryl groups, methyl or a substituted alkyl groups, preferably 2-cyanoethyl groups, and alkenyl groups.

The process according to the present invention can be carried out in solution. When such solution phase synthesis is employed, organic solvents which can be employed in the process of the present invention include haloalkanes, particularly dichloromethane, esters, particularly alkyl esters such as ethyl acetate, and methyl or ethyl propionate, amides such as dimethylformamide, N-methylpyrrolidinone and N,N'-dimethylimidazolidinone, and basic, nucleophilic solvents such as pyridine. Preferred solvents for the coupling and sulfur transfer steps are pyridine, dichloromethane and mixtures thereof, and particularly preferably pyridine. Organic solvents employed are preferably substantially anhydrous.

In certain embodiments of the present invention, the H-phosphonate or the alcohol, preferably the alcohol, is linked to a solid support. Most preferably, the alcohol linked to a solid support is a nucleoside or nucleotide having a free hydroxy group at the 5'-position, and is linked to the solid support via the 3'-position. Solid supports which may be employed are substantially insoluble in the solvent employed, and include those supports well known in the art for the solid phase synthesis of oligonucleotides. Examples include silica, controlled pore glass, polystyrene, copolymers comprising polystyrene such as polystyrene-poly(ethylene glycol) copolymers and polymers such as polyvinylacetate. Additionally, poly(acrylamide) supports, such as those more commonly employed for the solid phase synthesis of peptides may be employed if desired.

When a solid support is employed, the alcohol or H-phosphonate, most commonly the alcohol, is commonly bound to the solid support via a cleavable linker, preferably via the 3'-position. Examples of linkers that may be employed include those well known in the art for the solid phase synthesis of oligonucleotides, such as urethane, oxalyl, succinyl, and amino-derived linkers.

The process according to the present invention can be carried out by stirring a slurry of the alcohol or H-phosphonate bonded to the solid in a solution of the H-phosphonate or alcohol, respectively, coupling agent and sulphur-transfer agent. Alternatively, the solid support can be packed into a column, and a solution of H-phosphonate, coupling agent and sulfur transfer agent can be passed through the column.

When the H-phosphonate and the alcohol are both protected nucleosides or oligonucleotides, the invention provides an improved method for the stepwise and block synthesis of oligodeoxyribonucleotides, oligoribonucleotides and analogues thereof, based on H-phosphonate coupling reactions. According to one preferred aspect of the present invention, protected nucleosides or oligonucleotides with a 3'-terminal H-phosphonate function and protected nucleosides or oligonucleotides with a 5'-terminal hydroxy function are reacted in the presence of both a suitable coupling agent and a suitable sulfur-transfer agent, wherein a protected dinucleoside or oligonucleotide H-phosphonate intermediate is formed and said intermediates undergo sulfur-transfer by in situ reaction with the suitable sulfur-transfer agent.

In addition to the presence of hydroxy protecting groups, bases present in nucleosides/nucleotides employed in present invention are also preferably protected where necessary by suitable protecting groups. Organic bases which may be present include nucleobases, such as natural and unnatural nucleobases, and especially purines, such as hypoxanthine, and particularly A and G, and pyrimidines, particularly T, C and U. Protecting groups employed are those known in the art for protecting such bases. For example, A and/or C can be protected by benzoyl, including substituted benzoyl, for example alkyl- or alkoxy-, often $C_{1-4}$ alkyl- or $C_{1-4}$ alkoxy-, benzoyl; pivaloyl; and amidine, particularly dialkylaminomethylene, preferably di($C_{1-4}$-alkyl) aminomethylene such as dimethyl or dibutyl aminomethylene. G may be protected on O6 for example by a phenyl group, including substituted phenyl, for example 2,5-dichlorophenyl and also on N2 by for example an acyl group such as an isobutyryl group. T and U generally do not require protection, but in certain embodiments may advantageously be protected, for example at O4 by a phenyl group, including substituted phenyl, for example 2,4-dimethylphenyl or at N3 by a pivaloyloxymethyl, benzoyl, alkyl or alkoxy substituted benzoyl, such as $C_{1-4}$ alkyl- or $C_{1-4}$ alkoxybenzoyl.

When the alcohol and/or H-phosphonate is a protected nucleoside or oligonucleotide having protected hydroxy groups, one of the hydroxy protecting groups may be removed after carrying out the process of the invention in order to allow further coupling at that point. The protecting group removed and subsequent reactions carried out at that point will depend on the type of molecule being prepared. When the coupling is taking place in solution, the protecting group removed may be that on the 3'-hydroxy function. The oligonucleotide thus formed may be converted into an H-phosphonate and may then proceed through further couplings according to the process of the present invention, for example with a nucleoside or oligonucleotide comprising a 5'-hydroxy group, in the synthesis of a desired oligonucleotide sequence. Preferably, when the coupling is taking place in solution, the 5'-protecting group is removed. This may be converted to an H-phosphonate moiety and further coupled with a free hydroxy group, such as a 3'-hydroxy group. However, it is preferred that the deprotected 5'-hydroxy group is reacted with a nucleoside or oligonucleotide comprising a 3'-H phosphonate moiety. When the coupling is taking place using solid phase synthesis, preferably with an oligonucleotide linked to the solid support via the 3'-position, the protecting group removed is preferably at the 5'-position. The free 5'-hydroxy may be converted to an H-phosphonate moiety and employed in further couplings. However, it is most preferred that the free 5'-hydroxy is coupled with a nucleoside or oligonucleotide H-phosphonate, most preferably a 3' H-phosphonate. It will be recognised that corresponding reactions can be employed where an oligonucleotide is linked to a solid support via the 5' position. When required, free hydroxy groups can be converted to H-phosphonate moieties using methods known in the art for this purpose. When the desired couplings have been completed, the method may then proceed with steps to remove the protecting groups from the internucleotide linkages, the 3' and the 5'-hydroxy groups and from the bases, and, if appropriate, to separate the product from the solid support.

In a particularly preferred embodiment, the invention provides a method comprising the coupling of a 5'-O-(4,4'-dimethoxytrityl)-2'-deoxyribonucleoside or ribonucleoside 3'-H-phosphonate or a protected oligodeoxyribonucleotide or oligoribonucleotide 3'-H-phosphonate and a component with a free 5'-hydroxy function in the presence both of a suitable coupling agent and a suitable sulfur-transfer agent.

In the process of the present invention, any suitable coupling agents and sulfur-transfer agents available in the prior art may be used.

Examples of suitable coupling agents include alkyl and aryl acid chlorides, alkane and arene sulfonyl chlorides, alkyl and aryl chloroformates, alkyl and aryl chlorosulfites and alkyl and aryl phosphorochloridates.

Examples of suitable alkyl acid chlorides which may be employed include $C_2$ to $C_{16}$ alkanoyl chlorides, including linear and cyclic alkanoyl chlorides, and particularly pivaloyl chloride and adamantane carbonyl chloride. Examples of aryl acid chlorides which may be employed include substituted and unsubstituted benzoyl chlorides, such as $C_{1-4}$ alkoxy, halo, particularly fluoro, chloro and bromo, and $C_{1-4}$ alkyl, substituted benzoyl chlorides. When substituted, from 1 to 3 substituents are often present, particularly in the case of alkyl and halo substituents.

Examples of suitable alkanesulfonyl chlorides which may be employed include $C_1$ to $C_{16}$ alkanesulfonyl chlorides. Examples of arenesulfonyl chlorides which may be employed include substituted and unsubstituted benzenesulfonyl chlorides, such as $C_{1-4}$ alkoxy, halo, particularly fluoro, chloro and bromo, and $C_{1-4}$ alkyl, substituted benzenesulfonyl chlorides. When substituted, from 1 to 3 substituents are often present, particularly in the case of alkyl and halo substituents.

Examples of suitable alkyl chloroformates which may be employed include $C_2$ to $C_{16}$ alkyl chloroformates. Examples of aryl chloroformates which may be employed include substituted and unsubstituted phenyl chloroformates, such as $C_{1-4}$ alkoxy, halo, particularly fluoro, chloro and bromo, and $C_{1-4}$ alkyl, substituted phenyl chloroformates. When substituted, from 1 to 3 substituents are often present, particularly in the case of alkyl and halo substituents.

Examples of suitable alkyl chlorosulfites which may be employed include $C_1$ to $C_{16}$ alkyl chlorosulfites. Examples of aryl chlorosulfites which may be employed include substituted and unsubstituted phenyl chlorosulfites, such as $C_{1-4}$ alkoxy, halo, particularly fluoro, chloro and bromo, and $C_{1-4}$ alkyl, substituted phenyl chlorosulfites. When substituted, from 1 to 3 substituents are often present, particularly in the case of alkyl and halo substituents.

Examples of suitable alkyl phosphorochloridates which may be employed include di($C_1$ to $C_6$ alkyl) phosphorochloridates. Examples of aryl phosphorochloridates which may be employed include substituted and unsubstituted diphenyl phosphorochloridates, such as $C_{1-4}$ alkoxy, halo, particularly fluoro, chloro and bromo, and $C_{1-4}$ alkyl, substituted diphenyl phosphorochloridates. When substituted, from 1 to 3 substituents are often present, particularly in the case of alkyl and halo substituents.

Further coupling agents that may be employed are the chloro-, bromo- and (benzotriazo-1-yloxy)-phosphonium and carbonium compounds disclosed by Wada et al, in J.A.C.S. 1997, 119, pp 12710–12721 (incorporated herein by reference).

Preferred coupling agents are diaryl phosphorochloridates, particularly those having the formula (ArO)$_2$POCl wherein Ar is preferably phenyl, 2-chlorophenyl, 2,4,6-trichlorophenyl or 2,4,6-tribromophenyl.

The nature of the sulfur-transfer agent will depend on whether an oligonucleotide, a phosphorothioate analogue or a mixed oligonucleotide/oligonucleotide phosphorothioate is required. Sulfur transfer agents employed in the process of the present invention often have the general chemical formula:

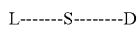

wherein L represents a leaving group, and D represents an aryl group, a methyl or a substituted alkyl group, preferably a 2-cyanoethyl group, or an alkenyl group. Commonly the leaving group is selected so as to comprise a nitrogen-sulfur bond. Examples of suitable leaving groups include imides such as morpholines such as morpholine-3,5-dione; phthalimides, succinimides and maleimides; indazoles, particularly indazoles with electron-withdrawing substituents such as 4-nitroindazoles; and triazoles.

Where a standard phosphodiester linkage is required in the final product, the sulfur transfer agent, the moiety D represents an aryl group, such as a phenyl or naphthyl group. Examples of suitable aryl groups include substituted and unsubstituted phenyl groups, particularly halophenyl and alkylphenyl groups, especially 4-halophenyl and 4-alkylphenyl, commonly 4-($C_{1-4}$ alkyl)phenyl groups, most preferably 4-chlorophenyl and p-tolyl groups. An example of a suitable class of standard phosphodiester-directing sulfur-transfer agent is an N-(arylsulfanyl)phthalimide, or an N-(arylsulfanyl)succinimide, for example N-(phenylsulfanyl)succinimide (or other imides, such as maleimides, may also be used).

Where a phosphorothioate diester linkage is required in the final product, the moiety D represents a methyl, substituted alkyl or alkenyl group. Examples of suitable substituted alkyl groups include substituted methyl groups, particularly benzyl and substituted benzyl groups, such as alkyl-, commonly $C_{1-4}$alkyl-, alkoxy-, commonly $C_{1-4}$alkoxy-, nitro, and halo-, commonly chloro-, substituted benzyl groups, and substituted ethyl groups, especially ethyl groups substituted at the 2-position with an electron-withdrawing substituent such as 2-(4-nitrophenyl)ethyl and 2-cyanoethyl groups. Examples of suitable alkenyl groups are allyl, crotyl and 4-cyanobut-2-enyl groups. Examples of a suitable class of phosphorothioate-directing sulfur-transfer agents are, for example, (2-cyanoethyl)sulfanyl derivatives such as 4-[(2-cyanoethyl)-sulfanyl]morpholine-3,5-dione or a corresponding reagent such as 3-(phthalimidosulfanyl) propanonitrile or more preferably 3-(succinimidosulfanyl) propanonitrile.

In many embodiments, the sulfur transfer agent is selected to react more rapidly with an H-phosphonate diester, particularly the H-phosphonate diester formed by the coupling of the H-phosphonate and the alcohol, than with an H-phosphonate monoester and/or the activated species formed by reaction of the H-phosphonate monoester with the coupling agent.

The process of the present invention can be conveniently carried out at a temperature in the range of from about −55° C. to about 35° C. Advantageously, the temperature is in the range of from about 0° C. to about 30° C. Most preferably, room temperature (commonly in the range of from 10 to 25° C., for example approximately 20–25° C.) is employed.

The mole ratio of H-phosphonate to alcohol in the process of the present invention is often selected to be in the range of from about 0.9:1 to 3:1, commonly from about 1:1 to about 2:1, and preferably from about 1.1:1 to about 1.5:1, such as about 1.2:1 when preparing dimers or about 1.4:1 when preparing larger units. However, where couplings on more than one free hydroxyl are taking place at the same time, the mole ratios will be increased proportionately. The mole ratio of coupling agent to alcohol is often selected to be in the range of from about 1:1 to about 10:1, commonly from about 1.5:1 to about 6:1 and preferably from about 2:1 to about 4:1. The mole ratio of sulfur transfer agent to alcohol is often selected to be in the range of from about 1:1 to about 10:1, commonly from about 1.5:1 to about 5:1 and preferably from about 2:1 to about 3:1.

In the process of the present invention, the H-phosphonate and the alcohol can be pre-mixed in solution, and a mixture of the coupling agent and sulfur-transfer agent can be added to this mixture. Reagent additions commonly take place continuously or incrementally over an addition period.

The concentrations of coupling agent and sulfur transfer agent employed in solution will often depend on the nature of the solvent employed. Concentrations up to 0.5M are commonly employed, for example, concentrations in the range of from 0.05M to 0.35M. In many embodiments, concentrations of sulfur transfer agent of about 0.2M, and concentrations of coupling agent of about 0.3M can be employed.

When either or both of the H-phosphonate and alcohol are employed as solutions, the concentration employed will depend on the nature of the solvent, and particularly on the molecular weight of the H-phosphonate or alcohol. Concentrations in the ranges described for coupling agents and sulfur transfer agents may be employed, although in many embodiments, concentrations of about 0.1M are employed.

In the process of the present invention, it is possible to prepare oligonucleotides containing both phosphodiester and phosphorothioate diester internucleotide linkages in the same molecule by selection of appropriate sulfur transfer agents, particularly when the process is carried out in a stepwise manner.

The process according to the present invention is preferably employed to produce oligonucleotides typically comprising 2 or more nucleotide residues. The upper limit will depend on the length of the oligonucleotide it is desired to prepare. Often, oligonucleotides produced by the process of the present invention comprise up to 40 nucleotide residues, commonly up to 35 nucleotide residues, and preferably from 5 to 25, such as from 8 to 20, nucleotide residues. The coupling and sulphur transfer steps of the process of the present invention are repeated a sufficient number of times to produce the desired length and sequence. The process of the present invention is especially suited for the preparation of oligonucleotides comprising 2, 3, 4, 5 or 6 nucleotide residues, and particularly dimers, trimers and tetramers.

As stated previously, the method of the invention can be used in the synthesis of RNA, 2'-O-alkyl-RNA, 2'-O-alkoxyalkyl-RNA and 2'-O-alkenyl-RNA sequences. 2'-O-(protecting group eg fpmp)-5'-O-(4,4-dimethoxytrityl)-ribonucleoside 3'-H-phosphonates 9 and 2'-O-(alkyl, alkoxyalkyl or alkenyl)-5'-O-(4,4-dimethoxytrityl)- ribonucleoside 3'-H-phosphonates 10a–c may be prepared, for example, from the corresponding protected nucleoside building blocks, ammonium p-cresyl H-phosphonate and pivaloyl chloride.

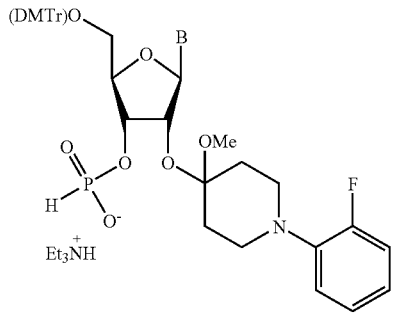

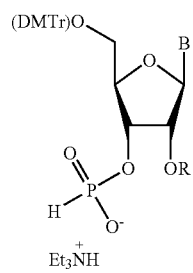

10a R = Me
10b R = CH$_2$CH═CH$_2$
10c R = CH$_2$CH$_2$OMe

For chemotherapeutically useful ribozyme sequences, relatively large scale RNA synthesis is a matter of considerable practical importance. The incorporation of 2'-O-alkyl, 2'-O-substituted alkyl and 2'-O-alkenyl [especially 2'-O-methyl, 2'-O-allyl and 2'-O-(2-methoxyethyl)]-ribonucleosides (Sproat, B. S. in 'Methods in Molecular Biology, Vol. 20. Protocols for Oligonucleotides and Analogs', Agrawal, S., Ed., Humana Press, Totowa, 1993) into oligonucleotides is currently a matter of much importance as these modifications confer both resistance to nuclease digestion and good hybridisation properties on the resulting oligomers.

The sulfur transfer step is carried out on the product of the H-phosphonate coupling in situ, ie without separation and purification of the intermediate produced by the coupling reaction. Preferably, the sulfur transfer agent is added at the same time as the coupling agent. The sulfur-transfer reagent employed and the coupling agent are both chosen to minimise side reactions, such that the rate of coupling is favoured over the rate of side reaction of the mono-ester H-phosphonate with the sulfur transfer agent. The choice of reagents is influenced by the nature of the H-phosphonate and alcohol which are to be coupled.

The present coupling procedure differs from that followed in the H-phosphonate approach to solid phase synthesis (Froehler et al., Methods in Molecular Biology, 1993) in that sulfur transfer is carried out at each coupling step rather than just once following the assembly of the whole oligomer sequence.

Protecting groups can be removed using methods known in the art for the particular protecting group and function. For example, transient protecting groups, particularly gamma keto acids such as levulinoyl-type protecting groups, can be removed by treatment with hydrazine, for example, buffered hydrazine, such as the treatment with hydrazine under very mild conditions disclosed by van Boom. J. H.; Burgers, P. M. J. *Tetrahedron Lett.*, 1976, 4875–4878. The resulting partially-protected oligonucleotides with free 3'-hydroxy functions may then be converted into the corresponding H-phosphonates which are intermediates which can be employed for the block synthesis of oligonucleotides and their phosphorothioate analogues.

When deprotecting the desired product once this has been produced, protecting groups on the phosphorus which produce phosphorothioate linkages are commonly removed first. For example, a cyanoethyl group can be removed by treatment with a strongly basic amine such as DABCO, 1,5-diazabicylo[4.3.0]non-5-ene (DBN), 1,8-diazabicyclo[5.4.0]undec-7-ene (DBU) or triethylamine.

Phenyl and substituted phenyl groups on the phosphorothioate internucleotide linkages and on the base residues can be removed by oximate treatment, for example with the conjugate base of an aldoxime, preferably that of E-2-nitrobenzaldoxime or pyridine-2-carboxaldoxime (Reese et al, Nucleic Acids Res. 1981). Kamimura, T. et al in *J. Am. Chem. Soc.*, 1984, 106 4552–4557 and Sekine, M. Et al, *Tetrahedron*, 1985, 41, 5279–5288 in an approach to oligonucleotide synthesis by the phosphotriester approach in solution, based on S-phenyl phosphorothioate intermediates; and van Boom and his co-workers in an approach to oligonucleotide synthesis, based on S-(4-methylphenyl) phosphorothioate intermediates (Wreesman, C. T. J. Et al, *Tetrahedron Lett.*, 1985, 26, 933–936) have all demonstrated that unblocking S-phenyl phosphorothioates with oximate ions (using the method of Reese et al., 1978; Reese, C. B,; Zard, L. *Nucleic Acids Res.*, 1981, 9, 4611–4626) led to natural phosphodiester internucleotide linkages. In the present invention, the unblocking of S-(phenyl)-protected phosphorothioates with the conjugate base of E-2-nitrobenzaldoxime proceeds smoothly and with no detectable internucleotide cleavage.

Other base protecting groups, for example benzoyl, pivaloyl and amidine groups can be removed by treatment with concentrated aqueous ammonia.

Trityl (including monomethoxy- and dimethoxy-trityl) groups present can be removed by treatment with acid. With regard to the overall unblocking strategy in oligodeoxyribonucleotide synthesis, another important consideration of the present invention, is that the removal of trityl, often a 5'-terminal DMTr, protecting group ('detritylation') should proceed without concomitant depurination, especially of any 6-N-acyl-2'-deoxyadenosine residues. According to an embodiment of the invention, the present inventors have found that such depurination, which perhaps is difficult completely to avoid in solid phase synthesis, can be totally suppressed by effecting 'detritylation' with a dilute solution of hydrogen chloride at low temperature, particularly ca. 0.45 M hydrogen chloride in dioxane-dichloromethane (1:8 v/v) solution at −50° C. Under these reaction conditions, 'detritylation' can be completed rapidly, and in certain cases after 5 minutes or less. For example, when 6-N-benzoyl-5'-O-(4,4'-dimethoxytrityl)-2'-deoxyadenosine was treated with hydrogen chloride in dioxane-dichloromethane under such conditions, 'detritylation' was complete after 2 min, but no depurination was detected even after 4 hours.

Silyl protecting groups may be removed by fluoride treatment, for example with a solution of a tetraalkyl ammonium fluoride salt such as tetrabutylammonium fluoride.

Fpmp protecting groups may be removed by acidic hydrolysis under mild conditions.

The process of the present invention can be employed for the preparation of oligonucleotide sequences with (a) solely phosphodiester, (b) solely phosphorothioate diester and (c) a combination of both phosphodiester and phosphorothioate diester internucleotide linkages.

It will be apparent that when the process of the present invention is applied to block synthesis, a number of alternative strategies are available in terms of the route to the desired product. These will depend on the nature of the desired product. For example, an octamer may be prepared by the preparation of dimers, coupled to produce tetramers, which are then coupled to produce the desired octamer. Alternatively, a dimer and a trimer may be coupled to produce a pentamer, which can be coupled with a further trimer to produce the desired octamer. The choice of strategy is at the discretion of the user. However, the common feature of such block coupling is that an oligomer H-phosphonate comprising two or more units is coupled with an oligomer alcohol also comprising two or more units. Most commonly oligonucleotide 3'-H-phosphonates are coupled with oligonucleotides having free 5'-hydroxy functions.

The process of the present invention can also be employed to prepare cyclic oligonucleotides, especially cyclic oligodeoxyribonucleotides and cyclic ribonucleotides. In the preparation of cyclic oligonucleotides, an oligonucleotide comprising an H-phosphonate function, often a 3' or 5' H-phosphonate, is prepared, and a free hydroxy function is introduced by appropriate deprotection. The position of the free hydroxy function is usually selected to correspond to the H-phosphonate, for example a 5' hydroxy function would be coupled with a 3' H-phosphonate, and a 3' hydroxy function would be coupled with a 5' H-phosphonate. The hydroxy and the H-phosphonate functions can then be coupled intramolecularly in solution in the presence of a coupling agent and this reaction is followed by in situ sulfur transfer.

The desired product, particularly a deprotected oligonucleotide, such as a deprotected oligonucleotide comprising solely phosphodiester or solely phosphorothioate internucleotide linkages, or a mixture of phosphodiester and at least one phosphorothiate internucleotide linkages, are advantageously purified by methods known in the art, such as one or more of ion-exchange chromatography, reverse phase chromatography, and precipitation from an appropriate solvent. Further processing of the product by for example ultrafiltration may also be employed.

The method according to the invention will now be illustrated with reference to the following examples which are not intended to be limiting:

In the Examples, it should be noted, that where nucleoside residues and internucleotide linkages are italicised, this indicates that they are protected in some way. In the present context, A, C, G, T and T (which is not italicised) represent 2'-deoxyadenosine protected on N-6 with a benzoyl group, 2'-deoxycytidine protected on N-4 with a benzoyl group, 2'-deoxyguanosine protected on N-2 and on O-6 with isobutyryl and 2,5-dichlorophenyl groups, thymine protected on O-4 with a phenyl group, and unprotected thymine. For example, as indicated in scheme 3, p(s) and p(s') represent S-(2-cyanoethyl) and S-(phenyl) phosphorothioates, respectively, and p(H), which is not protected and therefore not italicised, represents an H-phosphonate monoester if it is placed at the end of a sequence or attached to a monomer but otherwise it represents an H-phosphonate diester.

EXAMPLES

N-[(2-Cyanoethyl)sulfanyl]succinimide

N-Bromosuccinimide (17.80 g, 0.10 mol) and di-(2-cyanoethyl) disulfide (17.20 g, 0.10 mol) were heated, under reflux, in dry 1,2-dichloroethane (30 ml) in an atmosphere of argon for 2 hr. After the reaction mixture had been cooled down to room temperature, hexane (300 ml) was added and the mixture was stirred for 10 min. The upper layer was decanted and the oily residue was triturated with ethyl acetate (20 ml) for 10 min. The solid obtained was collected by filtration and washed with ether (70 ml) to give the title compound as an off-white solid (12.4 g, 67.3%) (found, in material recrystallized from absolute ethanol: C, 45.8; H, 4.3; N, 15.2. $C_7H_8N_2O_2S$ requires: C, 45.64; H, 4.38; N 15.21%), m.p. 110–b 112° C.; $\delta_H[(CD_3)_2SO]$ 2.71 (4 H, s), 2.75 (2 H, t, J 6.9), 3.02 (2 H, t, J 6.9); $\delta_C[(CD_3)_2SO]$ 17.9, 32.8, 118.2, 177.9.

N-(Phenylsulfanyl)succinimide

N-Bromosuccinimide (8.90 g, 50.0 mmol) and diphenyl disulfide (10.9 g, 49.9 mmol) were heated, under reflux, in dry 1,2-dichloroethane (40 ml) for 2 hr. After the reaction mixture had been cooled down to room temperature, hexane (150 ml) was added and the mixture was stirred for 30 min. The product was collected by filtration and washed with hexane (50 ml). Recrystallisation from absolute ethanol gave the title compound as colourless crystals (6.2 g, 59.8%), m.p. 110–112° C. (lit.[7] 115–b 116° C.); $\delta_H[(CD_3)_2SO]$ 2.84 (4 H, s), 7.32 (5 H, m); $\delta_C[(CD_3)_2SO]$ 28.8, 126.3, 127.6, 129.2, 135.3, 177.2.

Preparation of DMTr-Tp(s)T-Lev (B=B'=thymin-1-yl)

DMTr-Tp(H) (B=thymin-1-yl) (0.852 g, 1.2 mmol) and HO-T-Lev (B'=thymin-1-yl) (0.340 g, 1.0 mmol) were co-evaporated with dry pyridine (2 ml) and the residue was then redissolved in dry pyridine (6 ml) at room temperature. To this solution was added, dropwise over a period of 5 min, a solution of N-[(2-cyanoethyl)sulfanyl]succinimide (0.46 g, 2.5 mmol) and diphenyl phosphorochloridate (0.52 ml, 3.5 mmol) in dry pyridine (6 ml). After 5 min, water (1 ml) was added. The reaction mixture was then stirred for a further 5 min before partitioning between dichloromethane (50 ml) and saturated aqueous sodium hydrogen carbonate solution (50 ml). The organic layer was separated and then further washed with saturated aqueous sodium hydrogen carbonate solution (2×30 ml). The combined organic layers were dried ($MgSO_4$) and concentrated under reduced pressure. The residue was fractionated by short column chromatography on silica gel: evaporation of the appropriate fractions, which were eluted with $CH_2Cl_2$-MeOH (96:4 v/v) gave DMTr-Tp (s)T-Lev (B=B'=thymin-1-yl) as a colourless foam (1.009 g, 99.3%); $\delta_P[(CD_3)_2SO]$ 27.9, 27.7, 27.0 (ca. 0.7%).

Further examples of the process of the present invention were carried out by adding a solution of diphenyl phosphorochloridate 5b (2.5 mmol) and N-[(2-cyanoethyl)sulfanyl]- or N-(phenylsulfanyl)-succinimide (8a or 8b, 2.5 mmol) in anhydrous pyridine (6 ml) dropwise over a period of 5 min to a stirred solution of the H-phosphonate monomer (1.2 or 1.4 mmol) and the 5'-OH component (1.0 mmol) in anhydrous pyridine (6 ml) solution at room temperature. After a further period of 5–25 min (see total reaction time), the products were worked up and chromatographed. The results obtained are given in Table 1.

TABLE 1

| Entry no. | H-Phosphonate Monomer (mol. equiv) | 5'-OH Component | Coupling Agent | Sulfur-transfer Agent | Total Reaction Time (min) | Product Isolated Yield (%) | |
|---|---|---|---|---|---|---|---|
| 1 | DMTr-Tp (H) (1.2) | HO-T-Lev | 5b | 8a | 10 | DMTr-Tp(s)T-Lev | 99.3 |
| 2 | DMTr-Tp (H) (1.2) | HO-T-Lev | 5b | 8b | 10 | DMTr-Tp(s')T-Lev | 96.7 |
| 3 | DMTr-Tp (H) (1.2) | HO-T-Lev | 5b | 8a | 10 | DMTr-Tp(s)T-Lev | 97.6 |
| 4 | DMTr-Ap (H) (1.2) | HO-C-Lev | 5b | 8b | 10 | DMTr-Ap(s')C-Lev | 96.7 |
| 5 | DMTr-Cp (H) (1.2) | HO-G-LeV | 5b | 8a | 10 | DMTr-Cp(s)G-Lev | 97.0 |
| 6 | DMTr-Cp (H) (1.4) | HO-Tp(s)T-Lev | 5b | 8a | 30 | DMTr-Cp(s)Tp(s)T-Lev | 97.4 |
| 7 | DMTr-Gp (H) (1.4) | HO-Cp(s)G-Lev | 5b | 8a | 15 | DMTr-Gp(s)Cp(s)G-Lev | 97.0 |
| 8 | DMTr-Gp (H) (1.4) | HO-Cp(s)T-Lev | 5b | 8a | 30 | DMTr-Gp(s)Cp(s)T-Lev | 94.2 |
| 9 | DMTr-Tp (H) (1.4) | HO-Tp(s)T-Lev | 5b | 8a | 30 | DMTr-Tp(s)Tp(s)T-Lev | 95.1 |

What is claimed is:

1. In process for the preparation of a phosphorothioate triester which comprises coupling an H-phosphonate with an alcohol in the presence of a coupling agent thereby to form an H-phosphonate diester, and subsequently, reacting the H-phosphonate diester with a sulfur transfer agent thereby to form a phosphorothioate triester, the improvement wherein the coupling reaction between the H-phosphonate and the alcohol is carried out in the presence of the sulfur transfer agent which is later used to form the triester.

2. A process according to claim 1 wherein the H-phosphonate is a protected nucleoside or oligonucleotide comprising a 3'-H-phosphonate function.

3. A process according to either of claims 1 and 2, wherein the alcohol is a protected nucleoside or oligonucleotide comprising a free 5'-hydroxy function.

4. A process according to claim 1, wherein the coupling agent is a diaryl phosphorochloridate of formula (ArO)$_2$POCl, in which Ar represents phenyl, 2-chlorophenyl, 2,4,6-trichlorophenyl or 2,4,6-tribromophenyl.

5. A process according to claim 1, wherein the sulfur transfer agent has the general chemical formula:

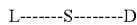

wherein L represents a leaving group, and D represents an aryl group, a methyl group, a substituted alkyl group or an alkenyl group.

6. A process according to claim 5, wherein the leaving group is a morpholine-3,5-dione, phthalimide, succinimide, maleimide or indazole, and D represents a 4-halophenyl group, 4-alkylphenyl group, methyl group, benzyl group, alkylbenzyl group, halobenzyl group, allyl group, crotyl group, 2-cyanoethyl group or a 2-(4-nitrophenyl)ethyl group.

7. A process according to claim 1, wherein the H-phosphonate and the alcohol are independently selected from the group consisting of deoxyribonucleosides, oligodeoxyribonucleosides, ribonucleosides, 2'-O-(alkyl, alkoxyalkyl or alkenyl)-ribonucleosides, oligoribonucleotides and 2'-O-(alkyl, alkoxyalkyl or alkenyl)-oligoribonucleotides.

8. A process according to claim 1, wherein the H-phosphonate or the alcohol is linked to a solid support.

9. A process according to claim 8, wherein an alcohol is linked to a solid support, the alcohol is a nucleoside or nucleotide having a free hydroxy group at the 5'-position, and is linked to the solid support via the 3'-position.

10. A process according to claim 8 or 9, wherein an alcohol linked to a solid support is contacted with a solution comprising an H-phosphonate, a coupling agent and a sulfur transfer agent.

11. A process according to claim 1, wherein the process is carried out in the solution phase.

12. A process according to claim 11, wherein a solution comprising the coupling agent and sulfur transfer agent is added to a solution comprising the H-phosphonate and the alcohol.

13. A process according to claim 1, wherein an oligonucleotide H-phosphonate and/or an oligonucleotide comprising a free 3' or 5'-hydroxy function is employed and either or both of the oligonucleotide H-phosphonate and the oligonucleotide comprising a free 3' or 5'-hydroxy function comprise one or more phosphorothioate internucleotide linkages.

14. A process according to claim 1, wherein the phosphorothioate triester comprises from 2 to 8 nucleotide residues.

15. A process for the preparation of a deprotected oligonucleotide, oligonucleotide phosphorothioate or mixed oligonucleotide/oligonucleotide phosphorothioate which comprises:

a) coupling a protected nucleoside or oligonucleotide H-phosphonate comprising a 3' or 5'-H-phosphonate function with a protected nucleoside or oligonucleotide comprising a free 3' or 5'-hydroxy function in the presence of a coupling agent thereby to form an H-phosphonate diester and, in situ, reacting the H-phosphonate diester with a sulfur transfer agent to produce a phosphorothioate triester, wherein the coupling reaction between the H-phosphonate and the alcohol, occurs in the presence of the sulfur transfer agent; and b) deprotecting the phosphorothioate triester produced in a) thereby to form a deprotected oligonucleotide, oligonucleotide phosphorothioate or mixed oligonucleotide, oligonucleotide/phosphorothioate.

16. A process according to claim 15, wherein the deprotected oligonucleotide, oligonucleotide phosphorothioate or mixed oligonucleotide/oligonucleotide phosphorothioate is subsequently purified.

17. A process according to claim 15, wherein the protected nucleoside or oligonucleotide H-phosphonate comprises a 3'-H-phosphonate function and the protected nucleoside or oligonucleotide comprising a free hydroxy function comprises a free 5'-hydroxy function.

18. A process according to claim 15, wherein the coupling agent is a diaryl phosphorochloridate of formula (ArO)$_2$POCl, in which Ar represents phenyl, 2-chlorophenyl, 2,4,6-trichlorophenyl or 2,4,6-tribromophenyl.

19. A process according to either of claims 15 or 16, wherein the sulfur transfer agent has the general chemical formula:

wherein L represents a leaving group, and D represents an aryl group, a methyl group, a substituted alkyl group or an alkenyl group.

20. A process according to claim 19, wherein the leaving group is a morpholine-3,5-dione, phthalimide, succinimide, maleimide or indazole, and D represents a 4-halophenyl group, 4-alkylphenyl group, methyl group, benzyl group, alkylbenzyl group, halobenzyl group, allyl group, crotyl group, 2-cyanoethyl group or a 2-(4-nitrophenyl)ethyl group.

21. A process according to claim 15, wherein an oligonucleotide H-phosphonate and/or an oligonucleotide comprising a free 3'- or 5'-hydroxy function is employed and either or both of the oligonucleotide H-phosphonate and the oligonucleotide comprising a free 3'- or 5'-hydroxy function comprise one or more phosphorothioate internucleotide linkages.

22. A process for the synthesis of a deprotected oligonucleotide, said process comprising an assembly process in which a protected oligonucleotide is assembled, and a deprotection process in which the deprotected oligonucleotide is produced, the assembly process comprising coupling of a protected nucleoside or oligonucleotide H-phosphonate with a protected nucleoside or oligonucleotide comprising a free hydroxy function in the presence of a coupling agent thereby to form an H-phosphonate diester, characterised in that the coupling of the protected nucleoside or oligonucleotide H-phosphonate with the protected nucleoside or oligonucleotide comprising a free hydroxy function occurs in the presence of the sulfur transfer agent.

23. A process according to claim 22, wherein the deprotected oligonucleotide is a phosphodiester oligonucleotide, phosphorothioate oligonucleotide or an oligonucleotide comprising both phosphodiester and phosphorothioate diester internucleotide linkages.

24. A process according to claim 22, wherein the protected nucleoside or oligonucleotide H-phosphonate comprises a 3'- or 5'-H-phosphonate group.

25. A process according to claim 22, wherein the protected nucleoside or oligonucleotide comprising a free hydroxy function comprises a free 3'- or 5'-hydroxy function.

26. A process according to claim 22, wherein the oligonucleotide is subsequently purified.

27. A process for the preparation of an H-phosphonate diester, which comprises coupling an H-phosphonate with an alcohol in the presence of a coupling agent, characterised in that the coupling reaction between the H-phosphonate and the alcohol occurs in the presence of the sulfur transfer agent.

28. A process according to claim 27, wherein the H-phosphonate is a protected nucleoside or oligonucleotide comprising a 3'-H-phosphonate function and the alcohol is a protected nucleoside or oligonucleotide comprising a free 5'-hydroxy function.

29. A process according to claim 8, wherein the alcohol is linked to the solid support.

30. A process according to claim 14, wherein the phosphorothioate triester comprises from 2 to 4 nucleotide residues.

* * * * *